US011696711B2

(12) United States Patent
Ivosevic et al.

(10) Patent No.: US 11,696,711 B2
(45) Date of Patent: Jul. 11, 2023

(54) BIOLOGICAL FLUID COLLECTION DEVICE

(71) Applicant: Becton, Dickinson and Company, Franklin Lakes, NJ (US)

(72) Inventors: Milan Ivosevic, Kinnelon, NJ (US); Bradley M. Wilkinson, North Haledon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 693 days.

(21) Appl. No.: 16/628,630

(22) PCT Filed: Jun. 21, 2018

(86) PCT No.: PCT/US2018/038779
§ 371 (c)(1),
(2) Date: Jan. 3, 2020

(87) PCT Pub. No.: WO2019/010008
PCT Pub. Date: Jan. 10, 2019

(65) Prior Publication Data
US 2020/0253521 A1    Aug. 13, 2020

Related U.S. Application Data

(60) Provisional application No. 62/529,148, filed on Jul. 6, 2017.

(51) Int. Cl.
*A61B 5/15*    (2006.01)
*A61B 5/00*    (2006.01)
*A61B 5/151*   (2006.01)

(52) U.S. Cl.
CPC .. *A61B 5/150022* (2013.01); *A61B 5/150114* (2013.01); *A61B 5/150122* (2013.01);
(Continued)

(58) Field of Classification Search
CPC ........ A61B 5/150022; A61B 5/150114; A61B 5/150122; A61B 5/150137;
(Continued)

(56) References Cited

U.S. PATENT DOCUMENTS

2004/0254599 A1* 12/2004 Lipoma ............ A61B 5/150259
606/181
2005/0216046 A1   9/2005 Yeoh et al.
(Continued)

FOREIGN PATENT DOCUMENTS

CN    1621101 A    6/2005
DE    69738420 T2  5/2008
(Continued)

*Primary Examiner* — Devin B Henson
(74) *Attorney, Agent, or Firm* — The Webb Law Firm

(57) ABSTRACT

A biological fluid collection device that includes a housing and a cartridge that is removably receivable within a portion of the housing is disclosed. The biological fluid collection device of the present disclosure allows for collection of capillary blood from a finger stick and provides a closed system that reduces the exposure of a blood sample. In one embodiment, a cartridge of the present disclosure also provides fast mixing of a blood sample with a sample stabilizer. In another embodiment, a cartridge of the present disclosure provides automatic plasma separation of the blood sample. Advantageously, once the cartridge is filled with a sample aid removed from the housing, the cartridge can be used for a variety of important purposes.

22 Claims, 12 Drawing Sheets

(52) U.S. Cl.
CPC .. *A61B 5/150137* (2013.01); *A61B 5/150748* (2013.01); *A61B 5/150755* (2013.01); *A61B 5/150763* (2013.01); *A61B 5/6826* (2013.01); *A61B 5/151* (2013.01); *A61B 5/150984* (2013.01)

(58) Field of Classification Search
CPC ........ A61B 5/150106; A61B 5/150748; A61B 5/150755; A61B 5/150763; A61B 5/150969; A61B 5/6826
See application file for complete search history.

(56) References Cited

U.S. PATENT DOCUMENTS

| | | | |
|---|---|---|---|
| 2009/0112125 A1 | 4/2009 | Tamir | |
| 2010/0168615 A1* | 7/2010 | Amano | A61B 5/1519 |
| | | | 600/583 |
| 2010/0261988 A1* | 10/2010 | Tamir | A61B 5/150519 |
| | | | 600/583 |
| 2014/0188002 A1 | 7/2014 | Close et al. | |
| 2014/0309557 A1* | 10/2014 | Fletcher | B01L 3/502 |
| | | | 600/583 |
| 2015/0044707 A1 | 2/2015 | Sanders | |
| 2016/0242689 A1 | 8/2016 | Roehr et al. | |
| 2016/0345884 A1 | 12/2016 | Tanaka | |
| 2017/0035337 A1 | 2/2017 | Wilkinson et al. | |
| 2019/0307383 A1* | 10/2019 | Spero | B01L 3/502715 |

FOREIGN PATENT DOCUMENTS

| | | |
|---|---|---|
| JP | 200761384 A | 3/2007 |
| JP | 2009542304 A | 12/2009 |
| JP | 201099437 A | 5/2010 |
| JP | 2014200477 A | 10/2014 |
| JP | 201712375 A | 1/2017 |
| WO | 0193762 A2 | 12/2001 |
| WO | 2008027319 A2 | 3/2008 |
| WO | 2008131920 A2 | 11/2008 |
| WO | 2010011805 A1 | 1/2010 |
| WO | 2014172245 A1 | 10/2014 |

* cited by examiner

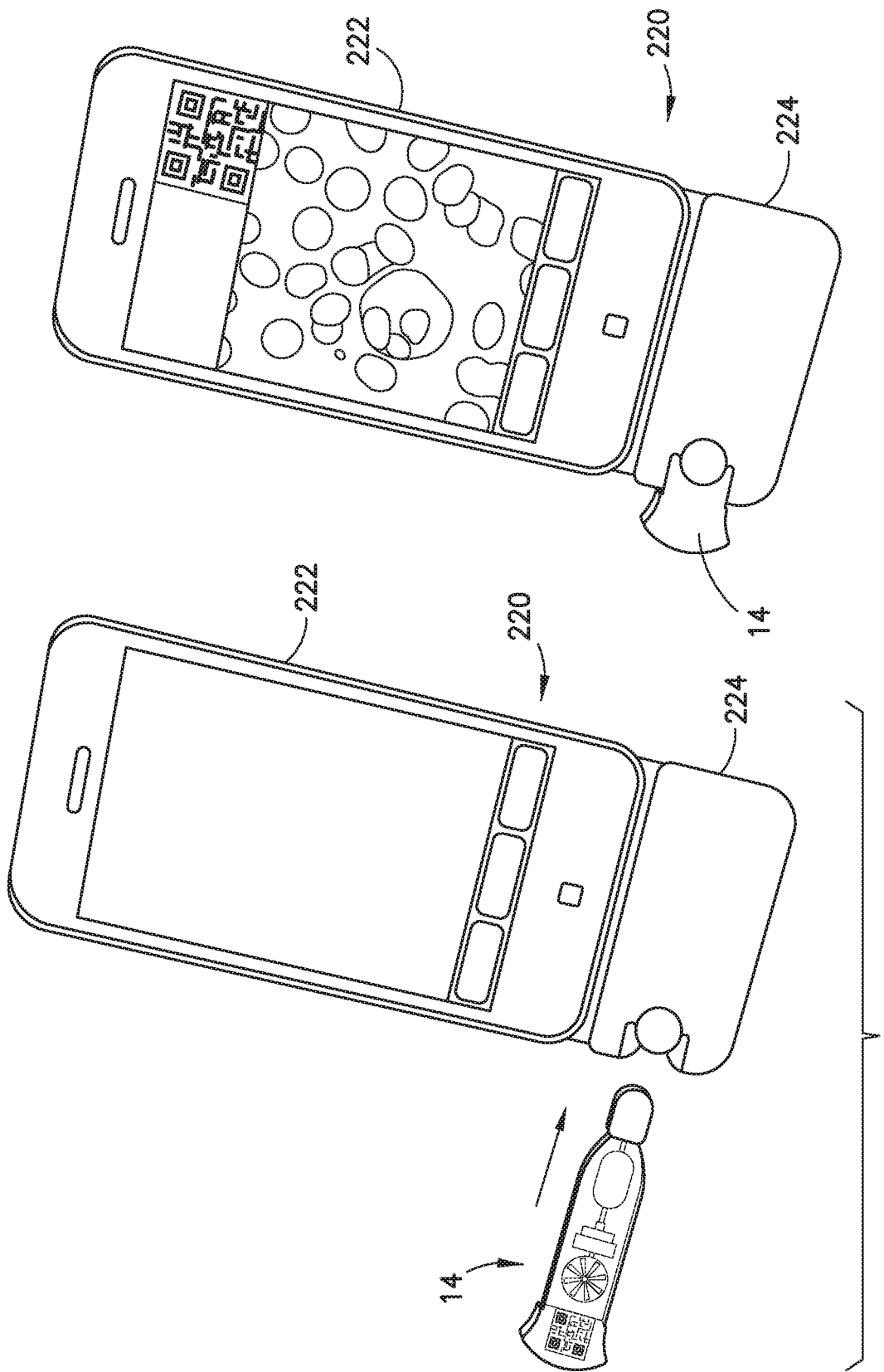

BIOLOGICAL FLUID COLLECTION DEVICE

CROSS-REFERENCE TO RELATED APPLICATION

This application is the United States national phase of International Application No. PCT/US2018/038779 filed Jun. 21, 2018, and claims priority to United States Provisional Patent Application No. 62/529,148 filed Jul. 6, 2017, the disclosures of which are hereby incorporated by reference in their entirety.

BACKGROUND OF THE INVENTION

1. Field of the Disclosure

The present disclosure relates generally to devices, assemblies, and systems adapted for blood collection. More particularly, the present disclosure relates to devices, assemblies, and systems adapted for finger based capillary blood collection.

2. Description of the Related Art

Blood sampling is a common health care procedure involving the withdrawal of at least a drop of blood from a patient. Blood samples are commonly taken from hospitalized, homecare, and emergency room patients either by finger stick, heel stick, or venipuncture. Blood samples may also be taken from patients by venous or arterial lines. Once collected, blood samples may be analyzed to obtain medically useful information including, for example, chemical composition, hematology, and coagulation.

Blood tests determine the physiological and biochemical states of the patient, such as disease, mineral content, drug effectiveness, and organ function. Blood tests may be performed in a clinical laboratory or at the point-of-care near the patient. One example of point-of-care blood testing is the routine testing of a patient's blood glucose levels which involves the extraction of blood via a finger stick and the mechanical collection of blood into a diagnostic strip or cartridge. Thereafter, the diagnostic cartridge, often using an associated instrument into which the strip or cartridge is inserted, analyzes the blood sample and provides the clinician a reading of the patient's blood glucose level. Other devices are available which analyze blood gas electrolyte levels, lithium levels, and ionized calcium levels. Some other point-of-care devices identify markers for acute coronary syndrome (ACS) and deep vein thrombosis/pulmonary embolism (DVT/PE).

Despite the rapid advancement in point-of-care testing and diagnostics, blood sampling techniques have remained relatively unchanged. Blood samples are frequently drawn using hypodermic needles or vacuum tubes attached to a proximal end of a needle or a catheter assembly. In some instances, clinicians collect blood from an already inserted vascularly located catheter assembly using a needle and syringe that is inserted into the catheter to withdraw blood from a patient through the inserted catheter. These procedures utilize needles and vacuum tubes as intermediate devices from which the collected blood sample is typically withdrawn prior to testing. These processes are thus device intensive, utilizing multiple devices in the process of obtaining, preparing, and testing blood samples. Each additional device increases the time and cost of the testing process.

Point-of-care testing devices allow for a blood sample to be tested without needing to send the blood sample to a lab for analysis. Thus, it is desirable to create a device that provides an easy, safe, reproducible, and accurate process with a point-of-care testing system.

SUMMARY OF THE INVENTION

The present disclosure provides a biological fluid collection device that includes a housing and a cartridge that is removably receivable within a portion of the housing. The biological fluid collection device of the present disclosure allows for collection of capillary blood from a finger stick and provides a closed system that reduces the exposure of a blood sample. In one embodiment, a cartridge of the present disclosure also provides fast mixing of a blood sample with a sample stabilizer. In another embodiment, a cartridge of the present disclosure provides automatic plasma separation of the blood sample. Advantageously, once the cartridge is filled with a sample and removed from the housing, the cartridge can be used for a variety of important purposes.

In accordance with an embodiment of the present invention, a biological fluid collection device includes a housing having an upper portion, a side portion, and a bottom portion, the upper portion having an inlet port and a cartridge receiving cavity; a puncturing element moveable between a pre-actuated position wherein the puncturing element is retained within a portion of the upper portion of the housing and a puncturing position wherein the puncturing element extends through the inlet port and provides fluid communication with a portion of the cartridge receiving cavity; and a cartridge having a reservoir, the cartridge removably receivable within the cartridge receiving cavity of the housing, the cartridge adapted to receive a blood sample therein, wherein, with the cartridge received within the cartridge receiving cavity, the inlet port is in fluid communication with a portion of the reservoir of the cartridge.

In one configuration, the upper portion, the side portion, and the bottom portion of the housing together form a C-shape. In another configuration, the upper portion, the side portion, and the bottom portion of the housing together define a finger receiving cavity. In yet another configuration, the upper portion includes a fill indicator window. In one configuration, the cartridge comprises an inlet and an outlet, the inlet and the outlet in fluid communication; a mixing chamber disposed between the inlet and the outlet; a sample stabilizer disposed between the inlet and the mixing chamber; and a collection chamber disposed between the mixing chamber and the outlet. In another configuration, the mixing chamber receives the blood sample and the sample stabilizer therein and the mixing chamber effectuates distributed mixing of the sample stabilizer within the blood sample. In yet another configuration, the cartridge includes an actuation portion, wherein the actuation portion is transitionable between a first position in which the blood sample is containable within the collection chamber and a second position in which a portion of the blood sample is expelled from the collection chamber. In one configuration, the actuation portion comprises a bulb. In another configuration, with the cartridge received within the cartridge receiving cavity, a portion of the collection chamber is aligned with the fill indicator window. In yet another configuration, the cartridge comprises an inlet and an outlet, the inlet and the outlet in fluid communication; a collection chamber disposed between the inlet and the outlet; and a separation member disposed between the inlet and the collection chamber, the separation member adapted to restrain a cellular portion of the blood sample and to allow a plasma portion of the blood sample to pass therethrough to the collection chamber. In one configuration, the cartridge includes an actuation portion, wherein the actuation portion is transitionable between a first position in which the blood sample is containable within the collection chamber and a second position in which a portion of the blood sample is expelled from the collection chamber. In another configuration, the actuation portion comprises a bulb. In yet another configuration, with the cartridge received within the cartridge receiving cavity, a portion of the collection chamber is aligned with the fill indicator window. In one configuration, the cartridge includes a readable information portion, wherein the readable information portion links the blood sample and patient identification. In another configuration, the readable information portion comprises a barcode. In yet another configuration, the cartridge includes qualitative onboard diagnostics. In one configuration, the cartridge includes quantitative onboard diagnostics. In another configuration, the biological fluid collection device includes an integrated pain reduction module. In one configuration, the integrated pain reduction module includes transcutaneous electrical nerve stimulation. In another configuration, the integrated pain reduction module includes heat. In yet another configuration, the integrated pain reduction module includes pressure. In one configuration, the integrated pain reduction module includes vibrations. In another configuration, the integrated pain reduction module includes chemical analgesics.

In accordance with another embodiment of the present invention, a biological fluid collection and testing system includes a biological fluid collection device, comprising: a housing having an upper portion, a side portion, and a bottom portion, the upper portion having an inlet port and a cartridge receiving cavity; a puncturing element moveable between a pre-actuated position wherein the puncturing element is retained within a portion of the upper portion of the housing and a puncturing position wherein the puncturing element extends through the inlet port and provides fluid communication with a portion of the cartridge receiving cavity; and a cartridge having a reservoir, the cartridge removably receivable within the cartridge receiving cavity of the housing, the cartridge adapted to receive a blood sample therein, wherein, with the cartridge received within the cartridge receiving cavity, the inlet port is in fluid communication with a portion of the reservoir of the cartridge, a near patient testing station having a receiving portion, wherein the cartridge is removably receivable within the receiving portion.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 13 is a perspective view of a cartridge of a biological fluid collection device being inserted into an interface for a smart phone for sample analysis in accordance with an embodiment of the present invention.

FIG. 14 is a perspective view of a cartridge of a biological fluid collection device received within an interface for a smart phone for sample analysis in accordance with an embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
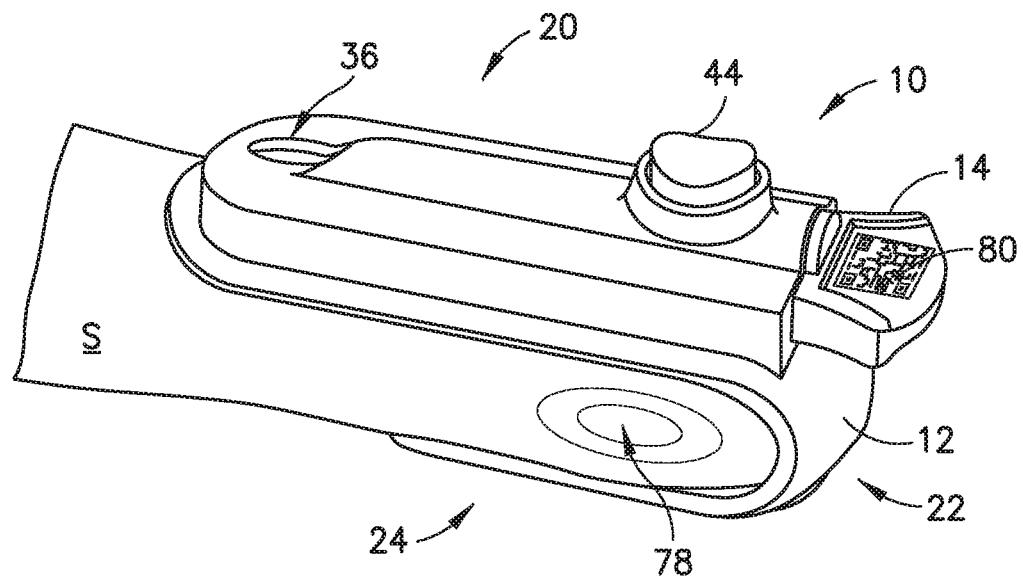
FIG. 1 is a perspective view of a biological fluid collection device secured to a finger of a patient in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

FIGS. 1-14 illustrate exemplary embodiments of the present disclosure. Referring to FIGS. 1-7, a biological fluid collection device 10 of the present disclosure includes a housing 12 and a cartridge 14 that is removably receivable within a portion of the housing 12. The biological fluid collection device 10 of the present disclosure allows for collection of capillary blood from a finger stick and provides a closed system that reduces the exposure of a blood sample. In one embodiment, a cartridge 14 of the present disclosure also provides fast mixing of a blood sample with a sample stabilizer. In another embodiment, a cartridge 14 of the present disclosure provides automatic plasma separation of the blood sample. Advantageously, once the cartridge 14 is filled with a sample and removed from the housing 12, the cartridge 14 can be used for a variety of important purposes.

Referring to FIGS. 1-9, the biological fluid collection device 10 of the present disclosure includes a housing 12 and a cartridge 14 that is removably receivable within a portion of the housing 12. The housing 12 includes an upper portion 20, a side portion 22, and a bottom portion 24. In one embodiment, the upper portion 20, the side portion 22, and the bottom portion 24 of the housing 12 together form a generally C-shape.

The upper portion 20 of the housing 12 includes a superior surface 26, an inferior surface 28, and defines a cartridge receiving cavity 30 therein. The upper portion 20 defines an opening 32 that allows for easy insertion and removal of a cartridge 14 with the cartridge receiving cavity 30. The inferior surface 28 of the upper portion 20 defines an inlet port 34. The superior surface 26 of the upper portion 20 defines a fill indicator window 36. The upper portion 20, the side portion 22, and the bottom portion 24 of the housing 12 together define a finger receiving cavity 38. The bottom portion 24 of the housing 12 includes a superior surface 27 and an inferior surface 29.

Figure 3A:
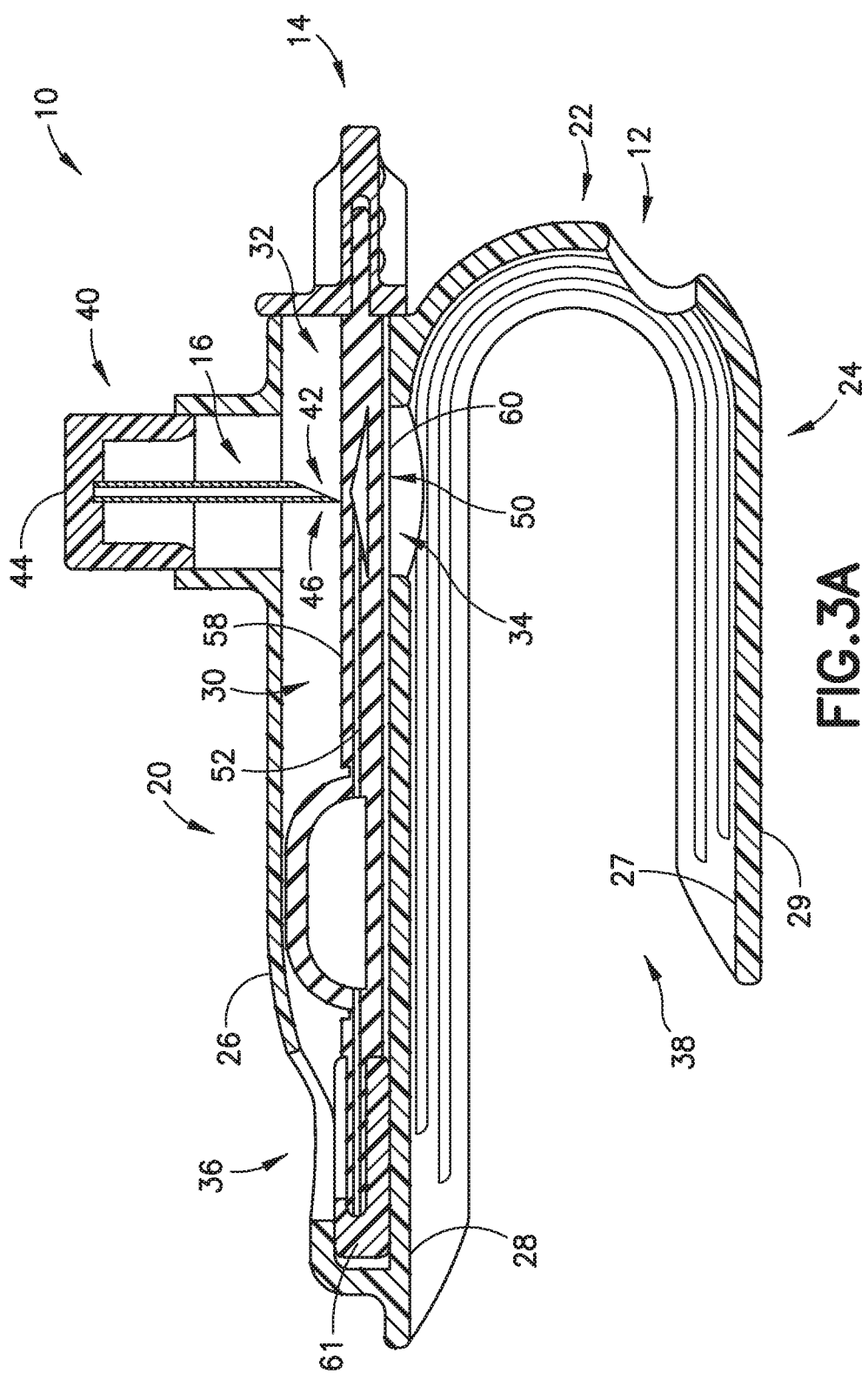
FIG. 3A is a cross-sectional view of the biological fluid collection device of FIG. 1 with a puncturing element in a pre-actuated position in accordance with an embodiment of the present invention.
Figure 3B:
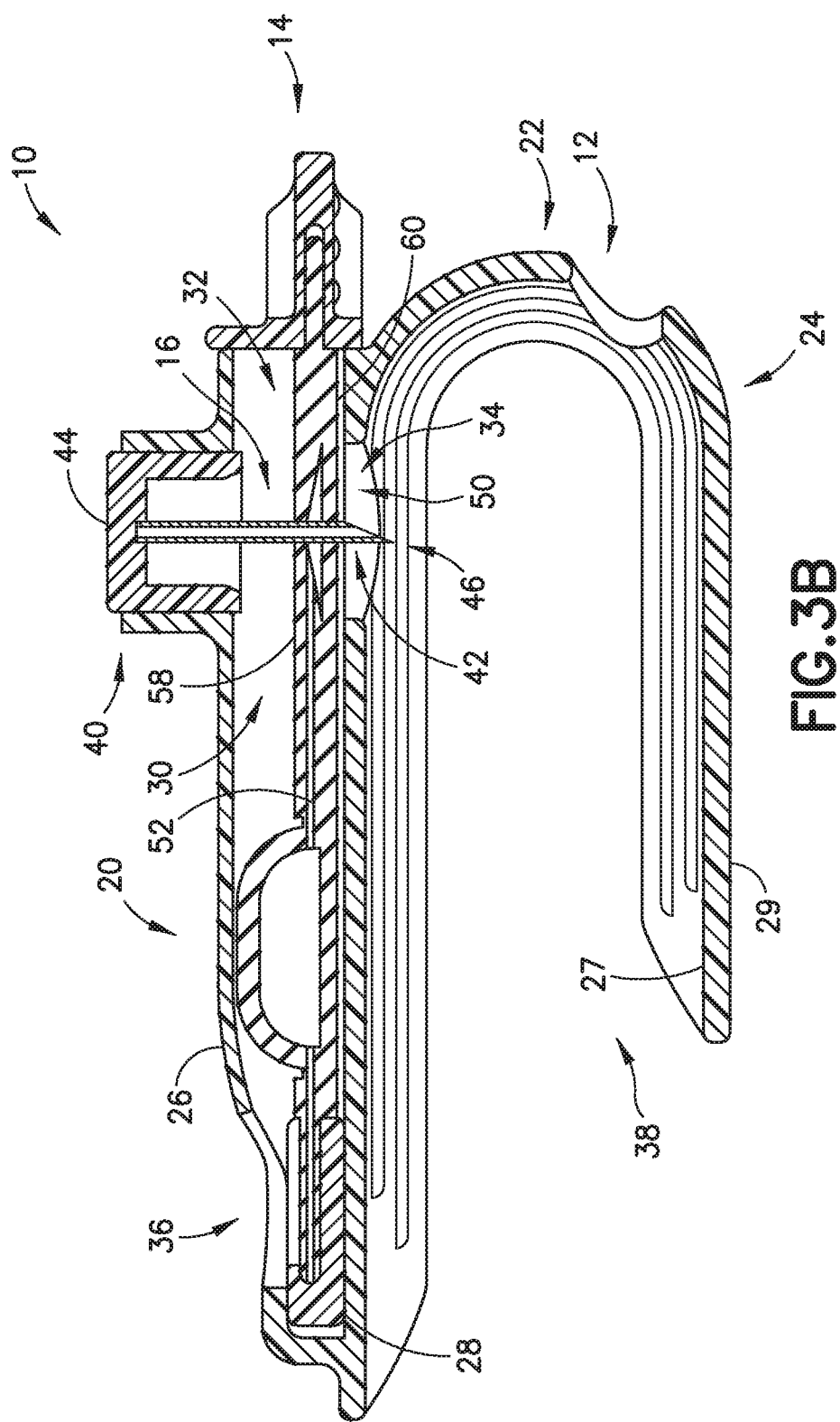
FIG. 3B is a cross-sectional view of the biological fluid collection device of FIG. 2 with a puncturing element in a puncturing position in accordance with an embodiment of the present invention.

Referring to FIGS. 3A-3B, the biological fluid collection device 10 also includes a puncturing element 16 that is positioned within a portion of the upper portion 20 of the housing 12. The puncturing element 16 generally includes a first end 40, a second end 42, a push button 44 adjacent the first end 40, and a puncturing end 46 adjacent the second end 42. In one embodiment, the first end 40 engages a portion of the upper portion 20 of the housing 12 and/or a portion of the push button 44 for securing the puncturing element 16 to a portion of the housing 12 as shown in FIGS. 3A-3B. The puncturing end 46 is adapted for puncturing a portion of a skin surface S of a patient, and may define a pointed end, a blade edge, or a similar cutting mechanism. The puncturing end 46 may include a preferred alignment orientation, such as with a pointed end of a blade aligned in a specific orientation. In one embodiment, the puncturing element 16 comprises a micro-needle array. In one embodiment, the puncturing element 16 is part of a retractable lancet device.

The puncturing element 16 is moveable within a portion of the housing 12 between a pre-actuated position (FIG. 3A) wherein the puncturing element 16 including the puncturing end 46 is retained within a portion of the upper portion 20 of the housing 12 and a puncturing position (FIG. 3B) wherein the puncturing end 46 of the puncturing element 16 extends through the inlet port 34 of the upper portion 20 of the housing 12 to puncture a skin surface S of a patient to draw a blood sample 18. In the puncturing position, the puncturing end 46 extends through the inlet port 34 and provides fluid communication with a portion of the cartridge receiving cavity 30. In one embodiment, actuation of the push button 44 moves the puncturing element 16 from the pre-actuated position to the puncturing position. In one embodiment, once the push button 44 is pressed, the puncturing end 46 of the puncturing element 16 punctures a portion of a skin surface S of a patient and then automatically retracts back to the shielded pre-actuated position.

With the puncturing element 16 in the pre-actuated position, the puncturing element 16 is configured to allow for easy insertion of the cartridge 14 within the cartridge receiving cavity 30 of the housing 12.

In one embodiment, the inferior surface 28 of the upper portion 20 and/or a superior surface 27 of the bottom portion 24 of the housing 12 includes an adhesive or adhesive layer to help secure the housing 12 of the biological fluid collection device 10 onto a skin surface S of a patient where a blood sample will be accessed. In one embodiment, the adhesive may be protected by a peel-off layer, similar to an adhesive bandage, which would be removed before placing the housing 12 of the biological fluid collection device 10 on the skin surface S of the patient's body. A hydrogel or other layer could be included to provide some thickness and help improve the stability of the adhesive seal. Additionally, in one embodiment, the adhesive could include a chemistry to create a more liquid-tight seal, similar to painter's tape technology, where wetting from the paint itself causes a chemical reaction with the adhesive to create a more water-tight barrier to prevent the paint from seeping under the tape. Importantly, the adhesive helps to provide proper adhesion of the housing 12 to the skin surface S of a patient and minimizes skin contact which leads to a better sample for coagulation testing. If needed, in some embodiments, the adhesive can be punctured by the puncturing element 16 such that the blood evolving from the wound beneath passes through the cut into the housing 12 to be collected inside a portion of the cartridge 14 of the biological fluid collection device 10.

Referring to FIGS. 1-9, the cartridge 14 includes an inlet 50, a first end 51, a reservoir 52, a second end 53, an outlet 54, an actuation portion 56, a superior surface 58, an inferior surface 60, an alignment portion 57, a securement portion 59, and a cap 61. The cartridge 14 is removably receivable within the cartridge receiving cavity 30 of the housing 12 as shown in FIGS. 1-7.

The cartridge 14 is adapted to receive a blood sample 18 therein. With the cartridge 14 received within the cartridge receiving cavity 30, the inlet port 34 of the housing 12 is in fluid communication with a portion of the reservoir 52 of the cartridge 14. For example, in one embodiment, with the cartridge 14 received within the cartridge receiving cavity 30, the inlet port 34 of the housing 12 is in fluid communication with the reservoir 52 of the cartridge 14 via the inlet 50 of the cartridge 14.

In one embodiment, the inlet 50 of the cartridge 14 includes a pierceable self-sealing portion on the superior surface 58 and the inferior surface 60 of the inlet 50. In this manner, with the cartridge 14 received within the cartridge receiving cavity 30 of the housing 12, and when the puncturing element 16 is moved to the puncturing position (FIG. 3B), the puncturing end 46 of the puncturing element 16 is able to pierce the self-sealing portions on the superior surface 58 and the inferior surface 60 of the inlet 50 so that the puncturing element 16 properly extends through the inlet 50 of the cartridge 14 and the inlet port 34 of the housing 12 thereby establishing fluid communication with a portion of the cartridge receiving cavity 30 of the housing 12, e.g., the inlet port 34, and a portion of the cartridge 14, e.g., the reservoir 52 of the cartridge 14 via the inlet 50.

In one embodiment, after the skin surface S of a patient is lanced, a sample is received within the cartridge 14, and the puncturing element 16 returns to the pre-actuated position (FIG. 3A), wherein the puncturing element 16 including the puncturing end 46 is retained within a portion of the upper portion 20 of the housing 12, the pierceable self-sealing portions automatically self-seal. In this manner, the pierceable self-sealing portions are capable of automatically self-sealing simultaneously with the puncturing end 46 of the puncturing element 16 being removed from the respective self-sealing portion. In one embodiment, the pierceable self-sealing portions comprise pierceable self-sealing stoppers.

In one embodiment, the first end 51 is adjacent the inlet 50 and the second end 53 is adjacent the outlet 54. The inlet 50 and the outlet 54 are in fluid communication. The actuation portion 56 of the cartridge 14 is transitionable between a first position (FIGS. 7 and 8) in which the blood sample 18 is containable within a portion of the reservoir 52 and a second position (FIG. 9) in which a portion of the blood sample 18 is expelled from the reservoir 52. In one embodiment, the actuation portion 56 comprises a bulb.

In one embodiment, the cap 61 protectively seals and covers the outlet 54 of the cartridge 14. The cap 61 is removably securable to the second end 53 of the cartridge 14. When it is desired to expel a portion of a blood sample 18 from the cartridge 14, the cap 61 is first removed.

In one embodiment, with the cartridge 14 received within the cartridge receiving cavity 30 of the housing 12, a portion of the reservoir 52 is aligned with the fill indicator window 36. In this manner, a visual indication is provided to a user to indicate when enough blood has been collected within the cartridge 14.

Figure 5:
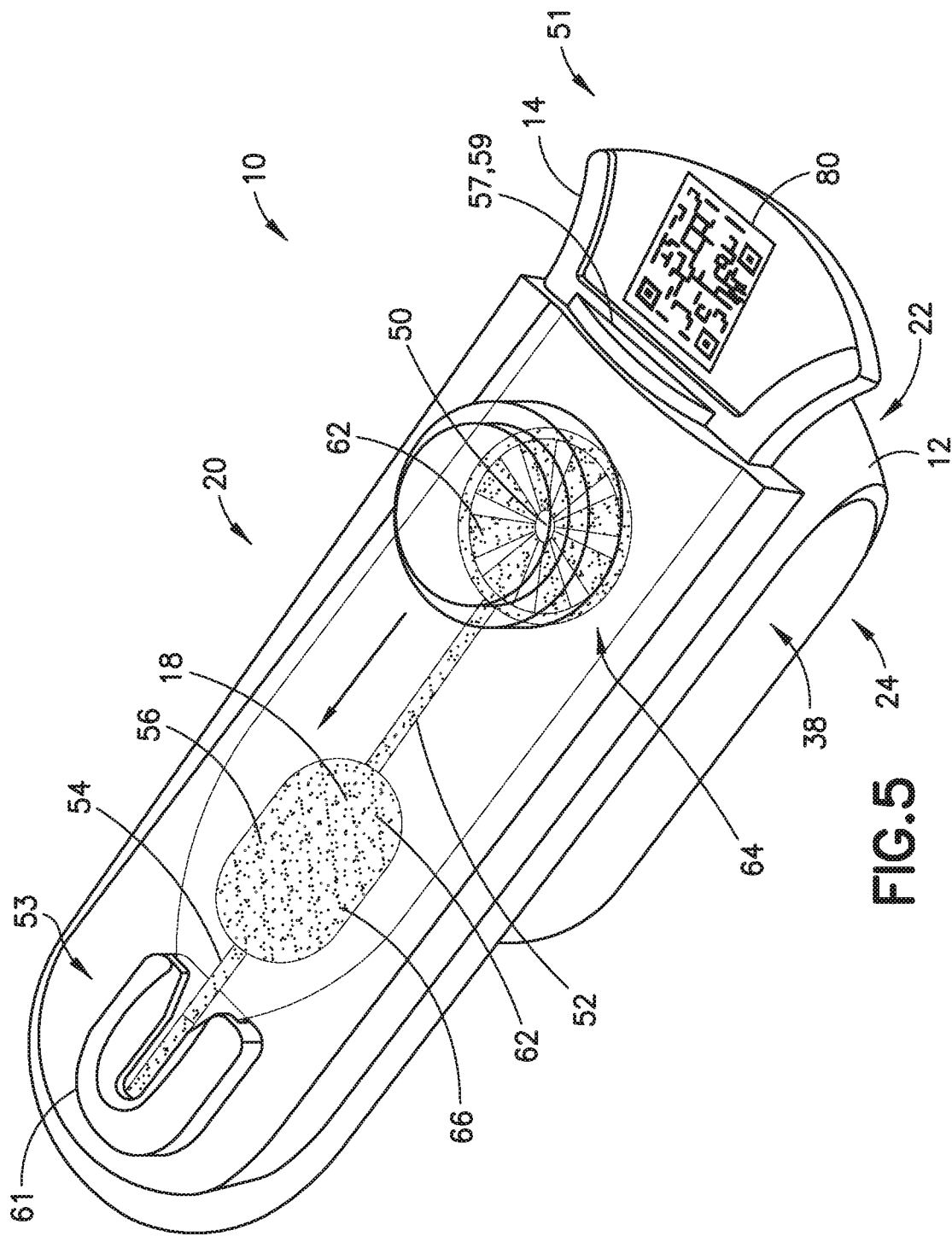
FIG. 5 is a perspective view of a biological fluid collection device with a cartridge of the device having a blood sample therein flowing to a collection chamber after mixing with a sample stabilizer in accordance with an embodiment of the present invention.
Figure 6:
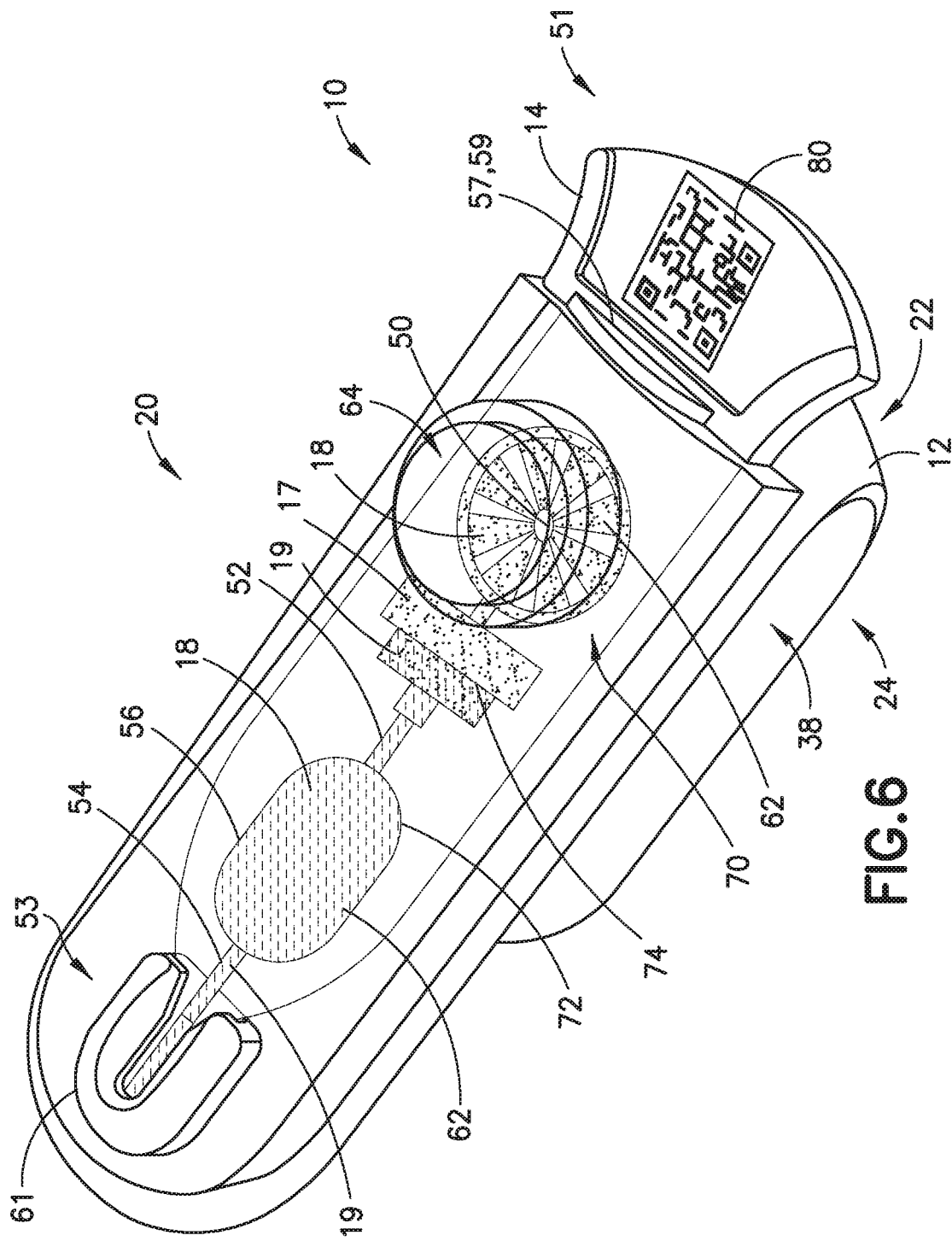
FIG. 6 is a perspective view of a biological fluid collection device with a cartridge of the device having a blood sample therein for automatic plasma separation in accordance with an embodiment of the present invention.
Figure 7:
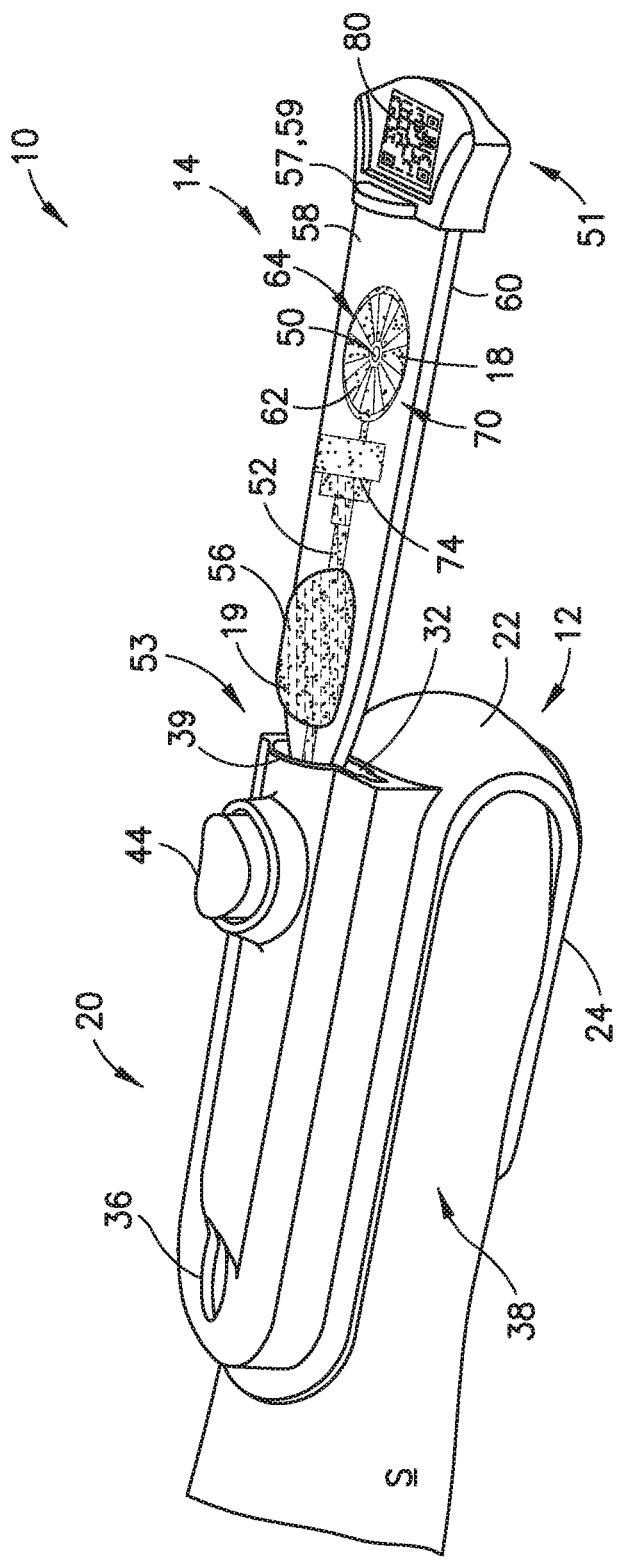
FIG. 7 is a perspective view of a biological fluid collection device secured to a finger of a patient and a cartridge being removed from a housing in accordance with an embodiment of the present invention.

As discussed above, the cartridge 14 is removably receivable within the cartridge receiving cavity 30 of the housing 12 as shown in FIGS. 1-7. Referring to FIG. 7, a user can grasp the first end 51 of the cartridge 14 to easily insert the cartridge 14 into the cartridge receiving cavity 30 of the housing 12 and to easily remove the cartridge 14 from the cartridge receiving cavity 30 of the housing 12. In one embodiment, the cartridge 14 may include a securement portion 59 to securely lock the cartridge 14 within the housing 12. For example, the securement portion 59 may releasably lock to a portion of the housing 12, e.g., a securement receiving portion 39 of the housing 12. In this manner, with the cartridge 14 received within the cartridge receiving cavity 30 of the housing 12, the cartridge 14 is locked relative to the housing 12, i.e., significant relative movement between the cartridge 14 and the housing 12 is prevented. Importantly, this ensures that during operation of the biological fluid collection device 10, the cartridge 14 is maintained in a proper position relative to the housing 12 and the puncturing element 16. This ensures that when the puncturing element 16 is moved to the puncturing position (FIG. 3B), the puncturing end 46 of the puncturing element 16 properly extends through the inlet 50 of the cartridge 14 and the inlet port 34 of the housing 12 thereby establishing fluid communication with a portion of the cartridge receiving cavity 30 of the housing 12, e.g., the inlet port 34, and a portion of the cartridge 14, e.g., the inlet 50. To remove the cartridge 14 from the cartridge receiving cavity 30 of the housing 12, a user can first release the engagement between the securement portion 59 of the cartridge 14 and the securement receiving portion 39 of the housing 12 and then grasp the first end 51 of the cartridge 14 to easily remove the cartridge 14 from the cartridge receiving cavity 30 of the housing 12.

In one embodiment, the cartridge 14 includes an alignment portion 57 that ensures the cartridge 14 is correctly orientated relative to the housing 12 and the puncturing element 16 when the cartridge 14 is inserted into the cartridge receiving cavity 30 of the housing 12.

Figure 4:
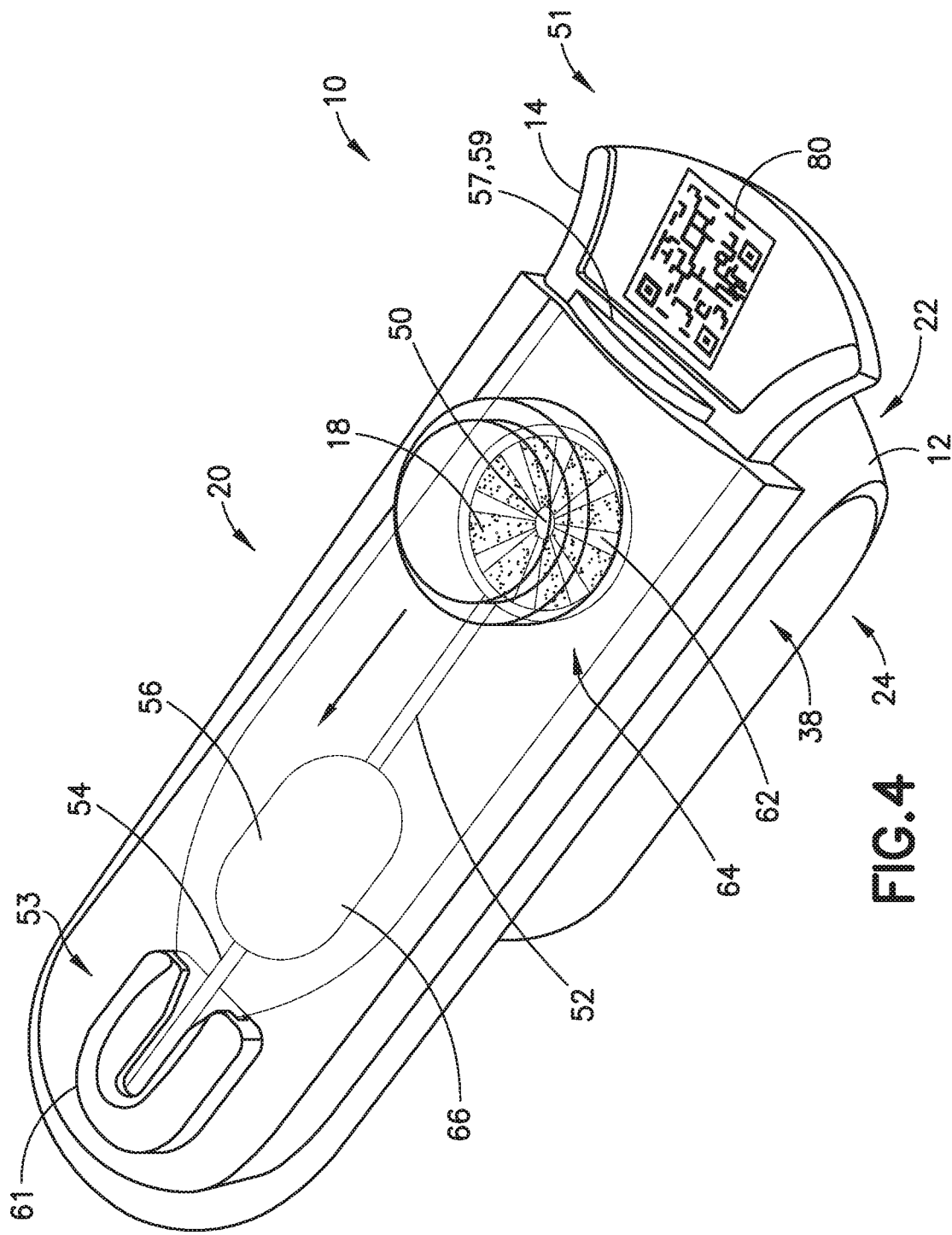
FIG. 4 is a perspective view of a biological fluid collection device with a cartridge of the device having a blood sample therein mixing with a sample stabilizer in accordance with an embodiment of the present invention.

Referring to FIGS. 4 and 5, in one embodiment, the cartridge 14 receives a blood sample 18 and provides flow-through blood stabilization technology and precise sample dispensing for point-of-care and near patient testing applications. The cartridge 14 is able to effectuate distributed mixing of a sample stabilizer 62 within a blood sample 18 and dispense the stabilized sample in a controlled manner. In this manner, the cartridge 14 enables blood microsample management, e.g., passive mixing with a sample stabilizer 62 and controlled dispensing, for point-of-care and near patient testing applications.

Referring to FIGS. 4 and 5, in one embodiment, the cartridge 14 includes a sample stabilizer 62, a mixing chamber 64, and a collection chamber 66. In one embodiment, the mixing chamber 64 is disposed between the inlet 50 and the outlet 54, the sample stabilizer 62 is disposed between the inlet 50 and the mixing chamber 64, and the collection chamber 66 is disposed between the mixing chamber 64 and the outlet 54.

In one embodiment, the mixing chamber 64 receives the blood sample 18 and the sample stabilizer 62 therein and the mixing chamber 64 effectuates distributed mixing of the sample stabilizer 62 within the blood sample 18. For example, the mixing chamber 64 effectuates distributed mixing of the sample stabilizer 62 within the sample 18 and prevents a very high sample stabilizer concentration in any portion of the blood sample 18. This prevents underdosing of the sample stabilizer 62 in any portion of the blood sample 18. The mixing chamber 64 effectuates distributed mixing of the sample stabilizer 62 within the sample 18 so that an approximately equal amount and/or concentration of the sample stabilizer 62 is dissolved throughout the blood sample 18, e.g., an approximately equal amount and/or concentration of the sample stabilizer 62 is dissolved into the blood sample 18 from a front portion of the blood sample 18 to a rear portion of the blood sample 18.

The sample stabilizer 62 can be an anticoagulant, or a substance designed to preserve a specific element within the blood such as, for example, RNA, protein analyte, or other element. In one embodiment, the sample stabilizer 62 is disposed between the inlet 50 and the mixing chamber 64. In other embodiments, the sample stabilizer 62 may be disposed in other areas within the cartridge 14.

After mixing, the stabilized sample flows to the collection chamber 66. In one embodiment, the actuation portion 56 is transitionable between a first position in which the blood sample 18 is containable within the collection chamber 66 and a second position in which a portion of the blood sample 18 is expelled from the collection chamber 66.

Blood transport within the cartridge 14 can be achieved via a plurality of ways. For example, in one embodiment, blood transport within the cartridge 14 can be passive, e.g., blood can be acquired and transferred by means of capillary force independent of hand or finger orientation. For example, in another embodiment, blood transport within the cartridge 14 can be active, e.g., blood can be acquired and transported by means of pressure differential generated by a vacuum source.

Referring to FIG. 5, in one embodiment, with the cartridge 14 received within the cartridge receiving cavity 30 of the housing 12, a portion of the collection chamber 66 is aligned with the fill indicator window 36. In this manner, a visual indication is provided to a user to indicate when enough of the stabilized sample has been collected within the collection chamber 66 of the cartridge 14.

Referring to FIG. 6, in one embodiment, the cartridge 14 receives a blood sample 18 and provides automatic plasma separation. For example, in one embodiment, the cartridge 14 receives a blood sample 18 having a cellular portion 17 and a plasma portion 19. After collecting the blood sample 18, the cartridge 14 is able to separate the plasma portion 19 from the cellular portion 17. After separation, the cartridge 14 is able to transfer the plasma portion 19 of the blood sample 18 to a point-of care testing device, a diagnostic cartridge, and/or other receiving ports. The cartridge 14 may provide integrated plasma separation by means of passive capillary or active pull of blood.

Referring to FIG. 6, in one embodiment, the cartridge 14 includes a first collection chamber 70, a second or plasma collection chamber 72, and a separation member or plasma separation section 74. In one embodiment, the separation member 74 is disposed between the inlet 50 and the plasma collection chamber 72 and the separation member 74 is adapted to restrain a cellular portion 17 of the blood sample 18 and to allow a plasma portion 19 of the blood sample 18 to pass therethrough to the plasma collection chamber 72. In one embodiment, the separation member 74 is disposed between the first collection chamber 70 and the plasma collection chamber 72 and the separation member 74 is adapted to restrain a cellular portion 17 of the blood sample 18 and to allow a plasma portion 19 of the blood sample 18 to pass therethrough to the plasma collection chamber 72.

After plasma separation, the plasma portion 19 can be transferred to a point-of care testing device 100 (FIG. 9), a diagnostic cartridge, and/or other receiving ports. In one embodiment, the actuation portion 56 is transitionable between a first position in which the plasma portion 19 is containable within the plasma collection chamber 72 and a second position in which a portion of the plasma portion 19 is expelled from the plasma collection chamber 72.

Referring to FIG. 6, in one embodiment, with the cartridge 14 received within the cartridge receiving cavity 30 of the housing 12, a portion of the plasma collection chamber 72 is aligned with the fill indicator window 36. In this manner, a visual indication is provided to a user to indicate when enough of the plasma portion 19 has been separated from the cellular portion 17 of the blood sample 18 and has been collected within the plasma collection chamber 72 of the cartridge 14.

In one embodiment, the separation member 74 may be either hollow fiber membrane filters commercially available, or flat membrane filters, such as track-etch filters commercially available. Membrane filter pore size and porosity can be chosen to optimize separation of clean (i.e., red blood cell free, white blood cell free, and platelet free) plasma in an efficient manner. In another embodiment, the separation member 74 may include a lateral flow membrane. In other embodiments, the separation member 74 may comprise any filter that is able to restrain the cellular portion 17 of the blood sample 18 and allow the plasma portion 19 of the blood sample 18 to pass through the separation member 74 to the plasma collection chamber 74. In other embodiments, the separation member 74 may comprise other separation components that allow the cartridge 14 to provide integrated plasma separation by means of passive capillary or active pull of blood.

Referring to FIG. 6, in one embodiment, the cartridge 14 receives a blood sample 18 and provides both flow-through blood stabilization technology and automatic plasma separation. In such an embodiment, the cartridge 14 is able to effectuate distributed mixing of a sample stabilizer 62 within a blood sample 18 and dispense the stabilized sample in a controlled manner. In this manner, the cartridge 14 enables passive mixing of a sample with a sample stabilizer 62 for point-of-care and near patient testing applications.

In such an embodiment, the cartridge 14 also provides automatic plasma separation. For example, in one embodiment, the cartridge 14 receives a blood sample 18 having a cellular portion 17 and a plasma portion 19. After collecting the blood sample 18, the cartridge 14 is able to separate the plasma portion 19 from the cellular portion 17. After separation, the cartridge 14 is able to transfer the plasma portion 19 of the blood sample 18 to a point-of care testing device, a diagnostic cartridge, and/or other receiving ports. The cartridge 14 may provide integrated plasma separation by means of passive capillary or active pull of blood.

In such an embodiment, the cartridge 14 includes a sample stabilizer 62, a mixing chamber 64, a first collection chamber 70, a second or plasma collection chamber 72, and a separation member or plasma separation section 74.

In one embodiment, the mixing chamber 64 is disposed between the inlet 50 and the first collection chamber 70. In one embodiment, the separation member 74 is disposed between the first collection chamber 70 and the plasma collection chamber 72 and the separation member 74 is adapted to restrain a cellular portion 17 of the blood sample 18 and to allow a plasma portion 19 of the blood sample 18 to pass therethrough to the plasma collection chamber 72.

In one embodiment, the mixing chamber 64 receives the blood sample 18 and the sample stabilizer 62 therein and the mixing chamber 64 effectuates distributed mixing of the sample stabilizer 62 within the blood sample 18. For example, the mixing chamber 64 effectuates distributed mixing of the sample stabilizer 62 within the sample 18 and prevents a very high sample stabilizer concentration in any portion of the blood sample 18. This prevents underdosing of the sample stabilizer 62 in any portion of the blood sample 18. The mixing chamber 64 effectuates distributed mixing of the sample stabilizer 62 within the sample 18 so that an approximately equal amount and/or concentration of the sample stabilizer 62 is dissolved throughout the blood sample 18, e.g., an approximately equal amount and/or concentration of the sample stabilizer 62 is dissolved into the blood sample 18 from a front portion of the blood sample 18 to a rear portion of the blood sample 18.

After mixing, the stabilized sample flows to the first collection chamber 70. Next, the stabilized sample having a cellular portion 17 and a plasma portion 19 is separated by the separation member 74 as described above. After plasma separation, the plasma portion 19 can be transferred to a point-of care testing device, a diagnostic cartridge, and/or other receiving ports. In one embodiment, the actuation portion 56 is transitionable between a first position in which the plasma portion 19 is containable within the plasma collection chamber 72 and a second position in which a portion of the plasma portion 19 is expelled from the plasma collection chamber 72.

In one embodiment, a biological fluid collection device 10 of the present disclosure includes an integrated pain reduction module that can provide pain reduction treatment to a patient, e.g., an exemplary pain reduction area 78 is shown in FIG. 1. In one embodiment, the integrated pain reduction module includes transcutaneous electrical nerve stimulation. In one embodiment, the integrated pain reduction module includes heat. In one embodiment, the integrated pain reduction module includes pressure. In one embodiment, the integrated pain reduction module includes vibrations. In one embodiment, the integrated pain reduction module includes chemical analgesics. The integrated pain reduction module of the present disclosure may include one or any combination of the above pain mitigation components. The integrated pain reduction module may be passive or achieved with a separate power source.

Figure 8:
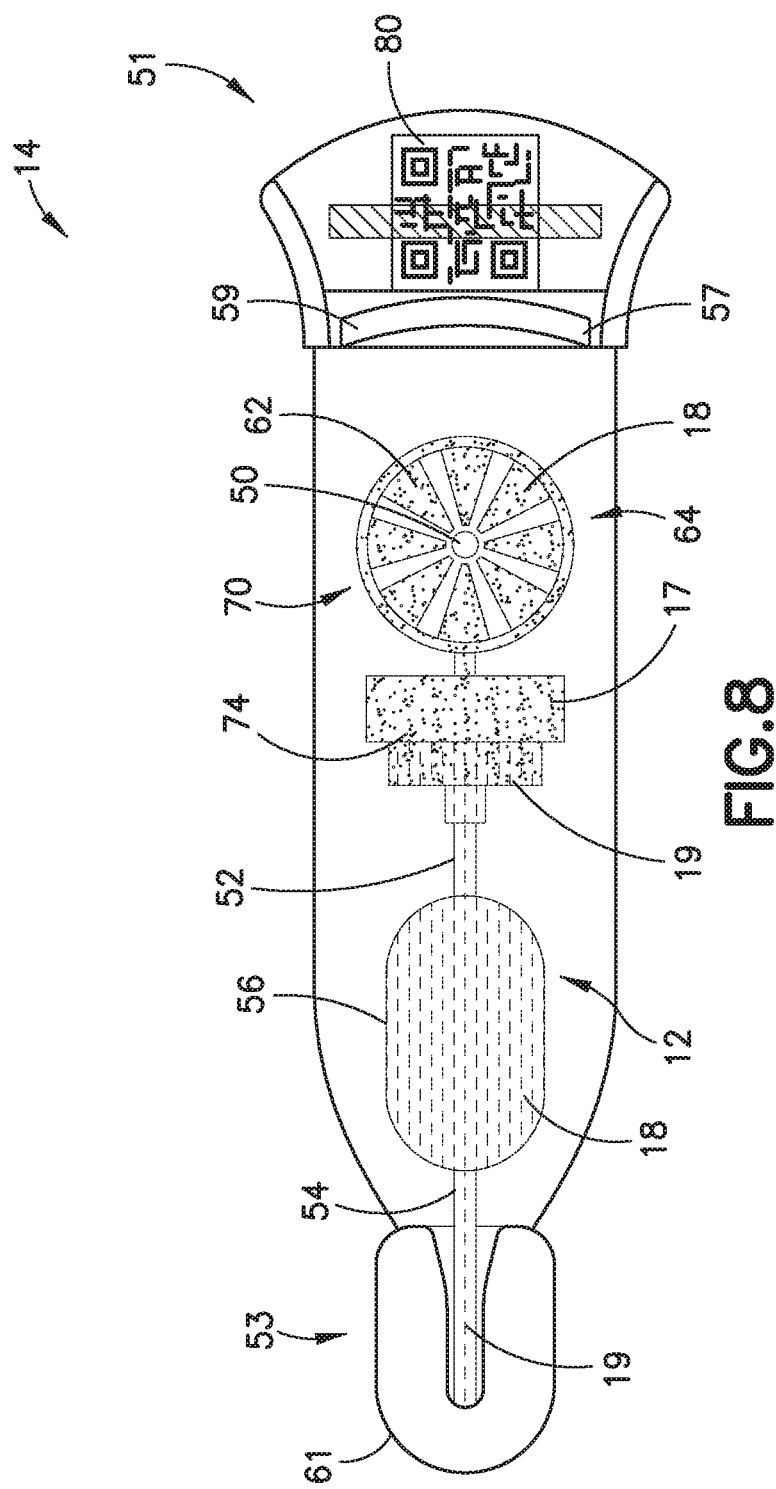
FIG. 8 is a perspective view of a cartridge of a biological fluid collection device having a readable information portion in accordance with an embodiment of the present invention.
Figure 9:
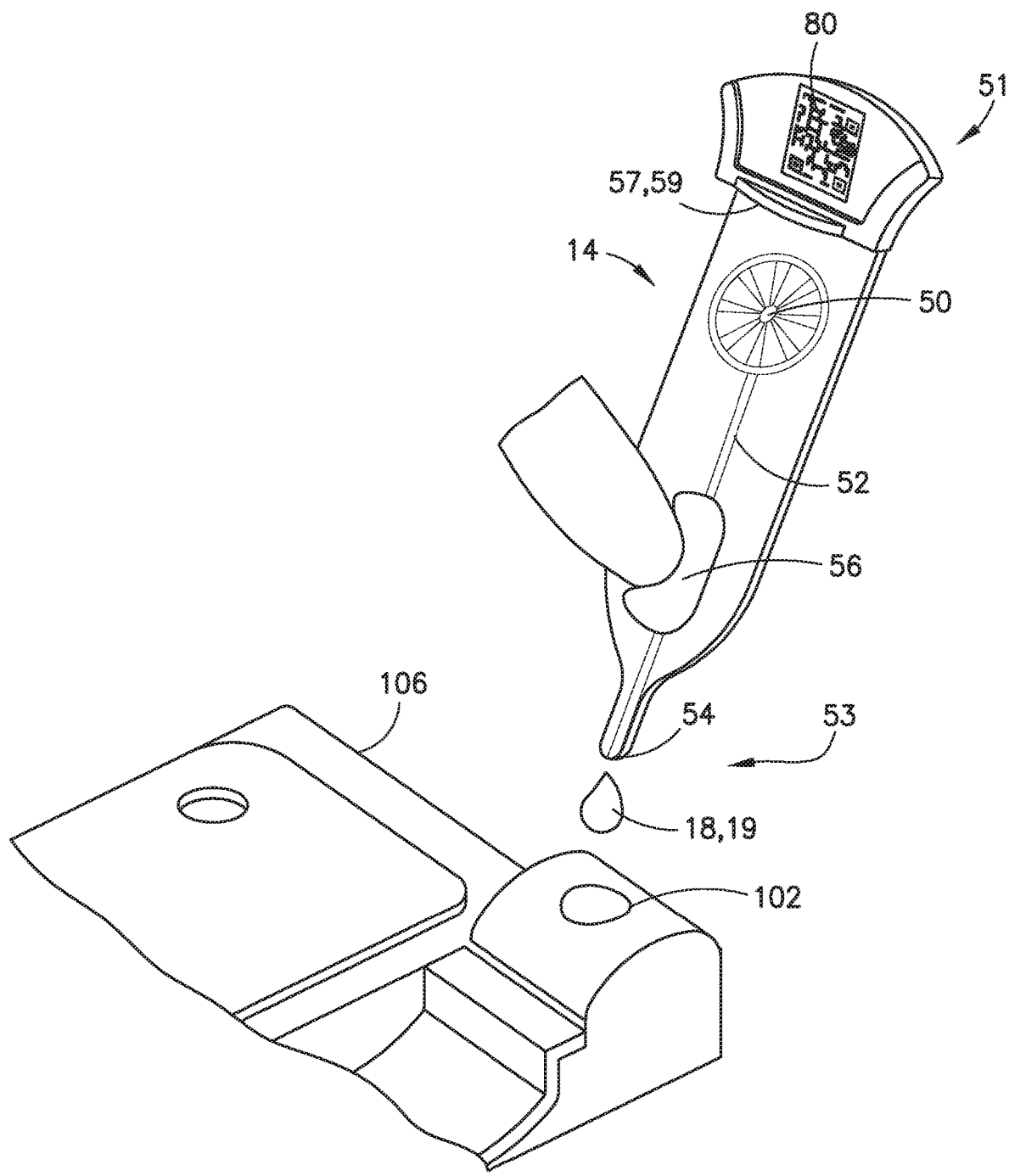
FIG. 9 is a perspective view of a cartridge of a biological fluid collection device being actuated to expel a portion of a blood sample to a point-of-care testing device in accordance with an embodiment of the present invention.

Referring to FIGS. 8 and 9, in one embodiment, the cartridge 14 includes a readable information portion 80. The readable information portion 80 is able to link a blood sample 18 and patient identification. For example, in one embodiment, the readable information portion 80 comprises a barcode. In such an embodiment, a patient sample can be identified by the barcode and thereby provide a unique link between the sample and patient identification.

In one embodiment, the readable information portion 80 is located on a portion of the first end 51 of the cartridge 14. In other embodiments, the readable information portion 80 may be located on other portions of the cartridge 14.

Referring to FIGS. 1-9, use of a biological fluid collection device 10 of the present disclosure will now be described. First, a cartridge 14 is selected and inserted within the cartridge receiving cavity 30 of the housing 12. With the cartridge 14 received within the cartridge receiving cavity 30 of the housing 12, the cartridge 14 is locked relative to the housing 12, i.e., significant relative movement between the cartridge 14 and the housing 12 is prevented. Importantly, this ensures that during operation of the biological fluid collection device 10, the cartridge 14 is maintained in a proper position relative to the housing 12 and the puncturing element 16.

A cartridge 14 can be selected that receives a blood sample 18 and provides both flow-through blood stabilization and automatic plasma separation. In such an embodiment, the cartridge 14 is able to effectuate distributed mixing of a sample stabilizer 62 within a blood sample 18 and dispense the stabilized sample in a controlled manner. In this manner, the cartridge 14 enables passive mixing of a sample with a sample stabilizer 62 for point-of-care and near patient testing applications. In such an embodiment, the cartridge 14 also provides automatic plasma separation. For example, in one embodiment, the cartridge 14 receives a blood sample 18 having a cellular portion 17 and a plasma portion 19. After collecting the blood sample 18, the cartridge 14 is able to separate the plasma portion 19 from the cellular portion 17. After separation, the cartridge 14 is able to transfer the plasma portion 19 of the blood sample 18 to a point-of care testing device, a diagnostic cartridge, and/or other receiving ports. The cartridge 14 may provide integrated plasma separation by means of passive capillary or active pull of blood. For other applications, a cartridge 14 can be selected that provides either blood stabilization or automatic plasma separation.

Referring to FIG. 1, upon selecting a site, a clinician or patient can then secure the housing 12 of the biological fluid collection device 10 to a patient's finger. In one embodiment, the inferior surface 28 of the upper portion 20 and/or a superior surface 27 of the bottom portion 24 of the housing 12 includes an adhesive or adhesive layer to help secure the housing 12 of the biological fluid collection device 10 onto a skin surface S of a patient where a blood sample will be accessed.

Figure 2:
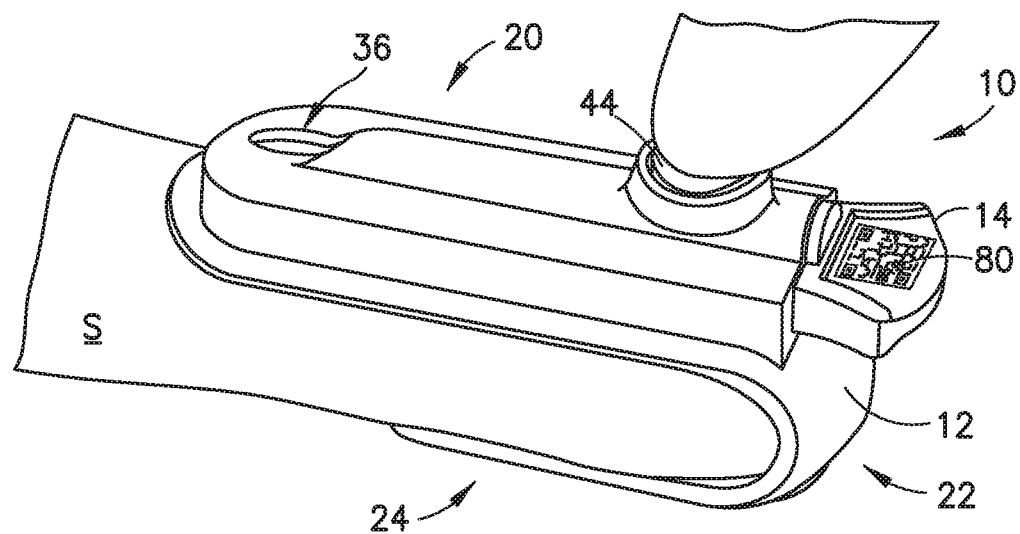
FIG. 2 is a perspective view of a biological fluid collection device secured to a finger of a patient and a puncturing element being actuated in accordance with an embodiment of the present invention.

Next, referring to FIG. 2, the push button 44 on the puncturing element 16 is depressed or actuated to move the puncturing element 16 from the pre-actuated position (FIG. 3A) to the puncturing position (FIG. 3B) so that the puncturing end 46 lances the skin surface S of a patient. In this position, the puncturing end 46 of the puncturing element 16 extends through the inlet 50 of the cartridge 14 and the inlet port 34 of the housing 12 thereby establishing fluid communication with a portion of the cartridge receiving cavity 30 of the housing 12, e.g., the inlet port 34, and a portion of the cartridge 14, e.g., the inlet 50.

After the push button 44 is depressed, the puncturing end 46 lances the skin and then automatically retracts back to the pre-actuated position (FIG. 3A). Upon puncturing the skin, blood flows into the cartridge 14 as described in detail above and as shown in FIGS. 4-6. As described above, with the cartridge 14 received within the cartridge receiving cavity 30 of the housing 12, a portion of the reservoir 52 is aligned with the fill indicator window 36. In this manner, a visual indication is provided to a user to indicate when enough blood has been collected within the cartridge 14.

When the reservoir 52 of the cartridge 14 is filled, the clinician or patient can remove the cartridge 14 from the housing 12 as shown in FIG. 7. When removed, the reservoir 52 of the cartridge 14 and all portions of the cartridge 14 are sealed from the external environment. In one embodiment, to remove the cartridge 14 from the cartridge receiving cavity 30 of the housing 12, a user can first release the engagement between the securement portion 59 of the cartridge 14 and the securement receiving portion 39 of the housing 12 and then grasp the first end 51 of the cartridge 14 to easily remove the cartridge 14 from the cartridge receiving cavity 30 of the housing 12 as shown in FIG. 7.

Advantageously, once the cartridge 14 is filled with a sample and removed from the housing 12, the cartridge 14 can be used for a variety of important purposes. Some of these advantageous uses of a cartridge 14 of the present disclosure will now be discussed.

Referring to FIGS. 8 and 9, in one embodiment, the cartridge 14 is able to transfer a portion of the blood sample 18 to a point-of-care testing device 100. Before dispensing, a patient can remove the cap 61 from the second end 53 of the cartridge. Next, a user can squeeze the actuation portion 56 of the cartridge 14 to expel a portion of the blood sample 18 from the cartridge 14. In one embodiment, referring to FIG. 9, a portion of the blood sample 18 can be expelled from the cartridge 14 to a receiving port 102 of a point-of-care testing device 100. The cartridge 14 allows for a single or multiple drops of a sample to be dispensed into one or more diagnostic cartridges or receiving ports and/or point-of-care testing devices.

In one embodiment, the cartridge 14 of the present disclosure is adapted to receive a blood sample 18 having a cellular portion 17 and a plasma portion 19. After collecting the blood sample 18, the cartridge 14 is able to separate the plasma portion 19 from the cellular portion 17 as discussed above. After separation, the cartridge 14 is able to transfer the plasma portion 19 of the blood sample 18 to a point-of-care testing device 100 as shown in FIG. 9.

Figure 10:
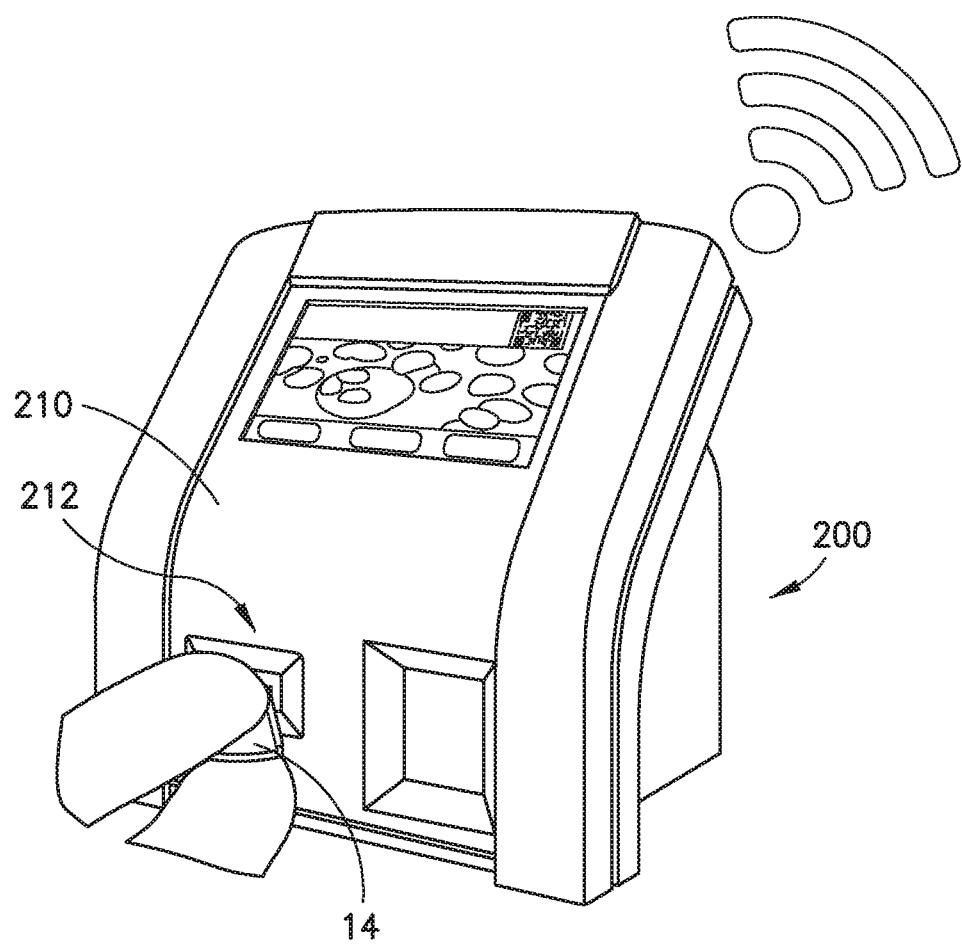
FIG. 10 is a perspective view of a cartridge of a biological fluid collection device being inserted into a near patient testing station in accordance with an embodiment of the present invention.

FIG. 10 illustrates another exemplary embodiment of the present disclosure. Referring to FIG. 10, a biological fluid collection and testing system 200 of the present disclosure includes a biological fluid collection device 10 having a housing 12 and a cartridge 14 that is removably receivable within a portion of the housing 12, as discussed above, and a near patient testing station 210. The near patient testing station 210 includes a receiving portion 212. The cartridge 14 is removably receivable within the receiving portion 212 of the near patient testing station 210. In one embodiment, the cartridge 14 comprises a disk or cartridge that can be directly inserted into the receiving portion 212 of the near patient testing station 210.

Advantageously, a cartridge 14 of the present disclosure being compatible with the near patient testing station 210 allows for convenient on-site sample analysis. In one embodiment, data can be transmitted wirelessly from the near patient testing station 210 to an intranet database.

FIGS. 13 and 14 illustrate another exemplary embodiment of the present disclosure.

Referring to FIGS. 13 and 14, a biological fluid collection and testing system 220 of the present disclosure includes a biological fluid collection device 10 having a housing 12 and a cartridge 14 that is removably receivable within a portion of the housing 12, as discussed above, and a hand-held instrument 222 and an interface 224. In one embodiment, the hand-held instrument 222 is a mobile device such as a smart phone.

Referring to FIGS. 13 and 14, the interface 224 is secured to a portion of the hand-held instrument 222. The interface 224 is in communication with the hand-held instrument 222. In one embodiment, the interface 224 may be a plug in attachment to the hand-held instrument 222. The cartridge 14 is removably receivable within the interface 224. In one embodiment, the cartridge 14 comprises a disk or cartridge that can be directly inserted into the interface 224.

Advantageously, a cartridge 14 of the present disclosure being compatible with the hand-held instrument 222 via the interface 224 allows for convenient sample analysis with a mobile device. In one embodiment, data can be transmitted wirelessly from the hand-held instrument 222 to an intranet database.

The hand-held instrument 222 allows a patient to use their mobile device as a point-of-care testing device. In this manner, a patient can conveniently utilize the benefits of a point-of-care testing device anywhere.

Figure 11:
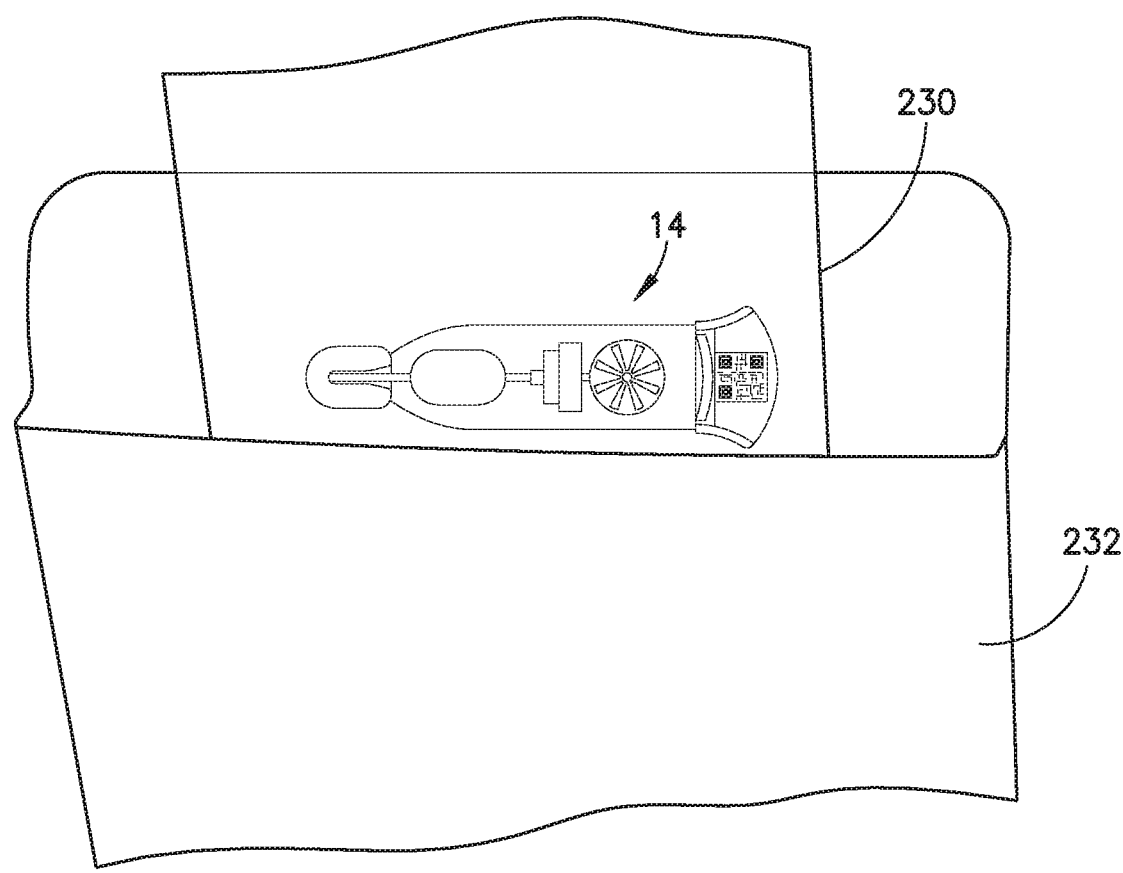
FIG. 11 is a perspective view of a cartridge of a biological fluid collection device being inserted into a mailing envelope for sending the cartridge to a lab for analysis in accordance with an embodiment of the present invention.

Referring to FIG. 11, another advantage of a biological fluid collection device 10 and cartridge 14 of the present disclosure is that after collecting a sample into the cartridge 14 and removing the cartridge 14 from the housing 12, the cartridge 14 can be placed into a protective packaging 230. In one embodiment, the cartridge 14 can be sealed within the protective packaging 230. Next, the protective packaging 230 with cartridge 14 can be placed in a mail envelope 232 and mailed to a lab for analysis. Typically blood may not be stable enough to ship via the mail. As discussed above, a cartridge 14 of the present disclosure is able to provide automatic plasma separation. This allows for the cartridge 14 to be mailed because the plasma is more stable and allows for collection at home and shipment to a lab for analysis.

Figure 12:
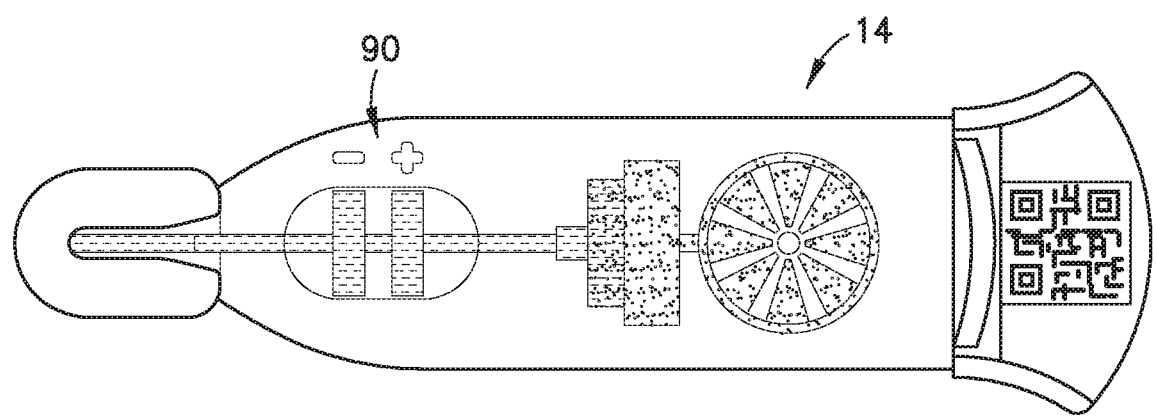
FIG. 12 is a perspective view of a cartridge of a biological fluid collection device having qualitative onboard diagnostics in accordance with an embodiment of the present invention.

Referring to FIG. 12, a biological fluid collection device 10 and cartridge 14 of the present disclosure also allows for additional advantages for at home screening tests. For example, referring to FIG. 12, in one embodiment, the cartridge 14 includes qualitative onboard diagnostics 90. In one embodiment, the cartridge 14 includes quantitative onboard diagnostics. In one embodiment, the cartridge 14 onboard diagnostics may include qualitative and/or quantitative by means of on-board sensors and/or color changing reagent. In this manner, a cartridge 14 of the present disclosure could be used similar to at home pregnancy tests. For example, a user could collect a sample at home and then based on the onboard diagnostics be informed a result based on a yes/no indicator, for example. In one embodiment, the onboard diagnostics provides a visual indication to let a user know if a result is positive or negative.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A biological fluid collection device, comprising:
a housing having an upper portion, a side portion, and a bottom portion, the upper portion having an inlet port and defining a cartridge receiving cavity, wherein the upper portion, the side portion, and the bottom portion of the housing together define a c-shaped cavity configured to receive a patient's finger therein;
a puncturing element moveable between a pre-actuated position wherein the puncturing element is retained within a portion of the upper portion of the housing and a puncturing position wherein the puncturing element extends through the inlet port and provides fluid communication with a portion of the cartridge receiving cavity;
a button arranged on the upper portion of the housing and coupled with the puncturing element; and
a cartridge having a reservoir and an inlet, the cartridge removably receivable within the cartridge receiving cavity of the housing, the inlet of the cartridge configured to be pierced by the puncturing element,
wherein the cartridge is adapted to receive a blood sample therein while the puncturing element is in the puncturing position,
wherein, with the cartridge received within the cartridge receiving cavity, the inlet port is in fluid communication with a portion of the reservoir of the cartridge, and
wherein the cartridge receiving cavity is arranged between the button and the c-shaped cavity.

2. The biological fluid collection device of claim 1, wherein the upper portion includes a fill indicator window.

3. The biological fluid collection device of claim 2, wherein the cartridge comprises:
an outlet, the inlet and the outlet in fluid communication;
a mixing chamber disposed between the inlet and the outlet;
a sample stabilizer disposed between the inlet and the mixing chamber; and
a collection chamber disposed between the mixing chamber and the outlet.

4. The biological fluid collection device of claim 3, wherein the mixing chamber receives the blood sample and the sample stabilizer therein and the mixing chamber effectuates distributed mixing of the sample stabilizer within the blood sample.

5. The biological fluid collection device of claim 3, wherein the cartridge includes an actuation portion, wherein the actuation portion is transitionable between a first position in which the blood sample is containable within the collection chamber and a second position in which a portion of the blood sample is expelled from the collection chamber.

6. The biological fluid collection device of claim 5, wherein the actuation portion comprises a bulb.

7. The biological fluid collection device of claim 3, wherein, with the cartridge received within the cartridge receiving cavity, a portion of the collection chamber is aligned with the fill indicator window.

8. The biological fluid collection device of claim 2, wherein the cartridge comprises:
- an outlet, the inlet and the outlet in fluid communication;
- a collection chamber disposed between the inlet and the outlet; and
- a separation member disposed between the inlet and the collection chamber, the separation member adapted to restrain a cellular portion of the blood sample and to allow a plasma portion of the blood sample to pass therethrough to the collection chamber.

9. The biological fluid collection device of claim 8, wherein the cartridge includes an actuation portion, wherein the actuation portion is transitionable between a first position in which the blood sample is containable within the collection chamber and a second position in which a portion of the blood sample is expelled from the collection chamber.

10. The biological fluid collection device of claim 9, wherein the actuation portion comprises a bulb.

11. The biological fluid collection device of claim 8, wherein, with the cartridge received within the cartridge receiving cavity, a portion of the collection chamber is aligned with the fill indicator window.

12. The biological fluid collection device of claim 1, wherein the cartridge includes a readable information portion, wherein the readable information portion links the blood sample and patient identification.

13. The biological fluid collection device of claim 12, wherein the readable information portion comprises a barcode.

14. The biological fluid collection device of claim 1, wherein the cartridge includes qualitative onboard diagnostics.

15. The biological fluid collection device of claim 1, wherein the cartridge includes quantitative onboard diagnostics.

16. The biological fluid collection device of claim 1, further comprising an integrated pain reduction module.

17. The biological fluid collection device of claim 16, wherein the integrated pain reduction module includes transcutaneous electrical nerve stimulation.

18. The biological fluid collection device of claim 16, wherein the integrated pain reduction module includes heat.

19. The biological fluid collection device of claim 16, wherein the integrated pain reduction module includes pressure.

20. The biological fluid collection device of claim 16, wherein the integrated pain reduction module includes vibrations.

21. The biological fluid collection device of claim 16, wherein the integrated pain reduction module includes chemical analgesics.

22. A biological fluid collection and testing system, comprising:
- a biological fluid collection device, comprising:
  - a housing having an upper portion, a side portion, and a bottom portion, the upper portion having an inlet port and a cartridge receiving cavity and wherein the upper portion, the side portion, and the bottom portion of the housing together define a c-shaped cavity configured to receive a patient's finger therein;
  - a puncturing element moveable between a pre-actuated position wherein the puncturing element is retained within a portion of the upper portion of the housing and a puncturing position wherein the puncturing element extends through the inlet port and provides fluid communication with a portion of the cartridge receiving cavity;
  - a button arranged on the upper portion of the housing and coupled with the puncturing element; and
  - a cartridge having a reservoir and an inlet, the inlet of the cartridge configured to be pierced by the puncturing element, and the cartridge removably receivable within the cartridge receiving cavity of the housing, the cartridge adapted to receive a blood sample therein while the puncturing element is in the puncturing position,
- wherein, with the cartridge received within the cartridge receiving cavity, the inlet port is in fluid communication with a portion of the reservoir of the cartridge,
- wherein the cartridge receiving cavity is arranged between the button and the c-shaped cavity; and
- a near patient testing station having a receiving portion, wherein the cartridge is removably receivable within the receiving portion.

* * * * *

UNITED STATES PATENT AND TRADEMARK OFFICE
CERTIFICATE OF CORRECTION

PATENT NO. : 11,696,711 B2
APPLICATION NO. : 16/628630
DATED : July 11, 2023
INVENTOR(S) : Milan Ivosevic et al.

It is certified that error appears in the above-identified patent and that said Letters Patent is hereby corrected as shown below:

On the Title Page

Column 2, Item (57) Abstract, Line 12, delete "aid" and insert -- and --

Signed and Sealed this
Twenty-ninth Day of August, 2023

Katherine Kelly Vidal
*Director of the United States Patent and Trademark Office*